US011051906B2

(12) United States Patent
Nardo et al.

(10) Patent No.: US 11,051,906 B2
(45) Date of Patent: Jul. 6, 2021

(54) ERGONOMIC BODY POSITIONING SYSTEM

(71) Applicant: American Sterilizer Company, Mentor, OH (US)

(72) Inventors: Richard P Nardo, Highland Heights, OH (US); Billy Odon M Yrad, Jr., Elyria, OH (US); Peter N Whitworth, Northfield, OH (US); Michael J Maczuzak, Bratenahl, OH (US)

(73) Assignee: American Sterilizer Company, Mentor, OH (US)

( * ) Notice: Subject to any disclaimer, the term of this patent is extended or adjusted under 35 U.S.C. 154(b) by 400 days.

(21) Appl. No.: 15/958,139

(22) Filed: Apr. 20, 2018

(65) Prior Publication Data
US 2018/0303575 A1    Oct. 25, 2018

Related U.S. Application Data

(60) Provisional application No. 62/489,156, filed on Apr. 24, 2017.

(51) Int. Cl.
*A61B 90/00* (2016.01)
*A61B 90/60* (2016.01)

(52) U.S. Cl.
CPC .................... *A61B 90/60* (2016.02)

(58) Field of Classification Search
CPC ................................ A47C 7/54; A47C 9/005
USPC .................. 248/121, 122.1, 118; 297/195.11
See application file for complete search history.

(56) References Cited

U.S. PATENT DOCUMENTS

| | | |
|---|---|---|
| 3,029,106 A | 4/1962 | McGuire |
| 3,477,673 A | 11/1969 | Bereday |
| 3,754,787 A | 8/1973 | Garber |
| 3,894,601 A | 7/1975 | Gestring |
| 3,917,203 A | 11/1975 | Heubeck et al. |
| 4,650,249 A | 3/1987 | Serber |
| 4,699,423 A | 10/1987 | Fitzig et al. |
| 4,867,273 A | 9/1989 | Schaevitz |
| 5,029,941 A | 7/1991 | Twisselmann |
| 5,295,728 A | 3/1994 | Schaevitz |
| 5,630,648 A | 5/1997 | Allard et al. |
| 5,927,815 A | 7/1999 | Nakamura et al. |
| 6,224,154 B1 | 5/2001 | Stoki |
| 6,619,747 B2 | 9/2003 | Ko et al. |
| 6,698,831 B2 | 3/2004 | Lloyd |
| 6,926,365 B2 | 8/2005 | Bottoms |
| 6,957,718 B1 | 10/2005 | Whiteside et al. |

(Continued)

FOREIGN PATENT DOCUMENTS

| | | |
|---|---|---|
| DE | 296 00 203 U1 | 3/1996 |
| FR | 2 207 417 A5 | 6/1974 |

OTHER PUBLICATIONS

International Search Report and Written Opinion issued in related PCT/US2018/028811 dated Jul. 6, 2018.

(Continued)

*Primary Examiner* — Steven M Marsh
(74) *Attorney, Agent, or Firm* — Kusner & Jaffe

(57) ABSTRACT

An ergonomic body positioning system for supporting and positioning a user such that the user can maintain a neutral body position while providing improved access and visibility to a worksite. The body positioning system includes a base, a support arm, a stem mounted to the support arm, and at least one body support device.

17 Claims, 17 Drawing Sheets

(56) References Cited

U.S. PATENT DOCUMENTS

| | | | |
|---|---|---|---|
| 7,093,900 B1 | 8/2006 | Schon | |
| 7,140,691 B2 | 11/2006 | Kohani | |
| 7,618,090 B2 | 11/2009 | Grenon | |
| 7,810,767 B1 | 10/2010 | Harris | |
| 8,480,168 B2 | 7/2013 | Turner et al. | |
| 8,496,292 B2 | 7/2013 | Strassberg | |
| 9,027,710 B2 | 5/2015 | Machovic Basic et al. | |
| 9,161,819 B2 | 10/2015 | Magelund et al. | |
| 9,314,390 B2 * | 4/2016 | Hernandez | A61G 13/1235 |
| 9,451,831 B2 | 9/2016 | Richardson et al. | |
| 2002/0158492 A1 * | 10/2002 | Ko | A47C 7/54 |
| | | | 297/112 |
| 2006/0207021 A1 | 9/2006 | Brunson et al. | |
| 2007/0007400 A1 * | 1/2007 | James | A47C 9/025 |
| | | | 248/125.1 |
| 2007/0246990 A1 | 10/2007 | Grenon | |
| 2008/0079230 A1 * | 4/2008 | Graham | A61G 5/0816 |
| | | | 280/87.041 |
| 2009/0278391 A1 | 11/2009 | Ulrich | |
| 2011/0163577 A1 | 7/2011 | Anastasov | |
| 2014/0265496 A1 * | 9/2014 | Magelund | A61B 90/60 |
| | | | 297/313 |
| 2015/0123432 A1 | 5/2015 | Ray | |

OTHER PUBLICATIONS

Examination Report issued in corresponding Australian Patent Application No. 2018260619 dated Oct. 24, 2019.
Extended European Search Report issued in related European Application No. 18791262.1 dated Dec. 17, 2020.

\* cited by examiner

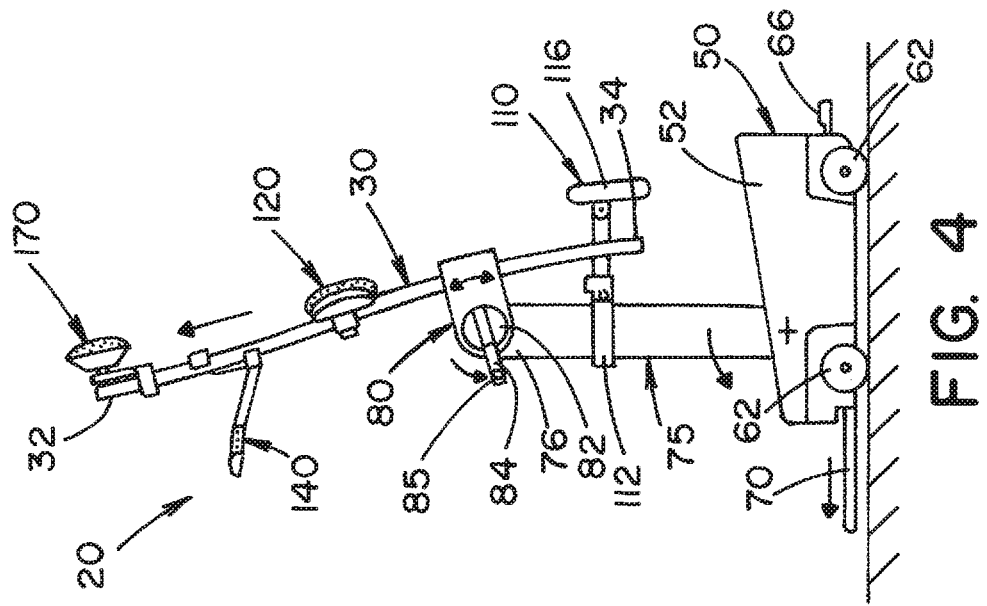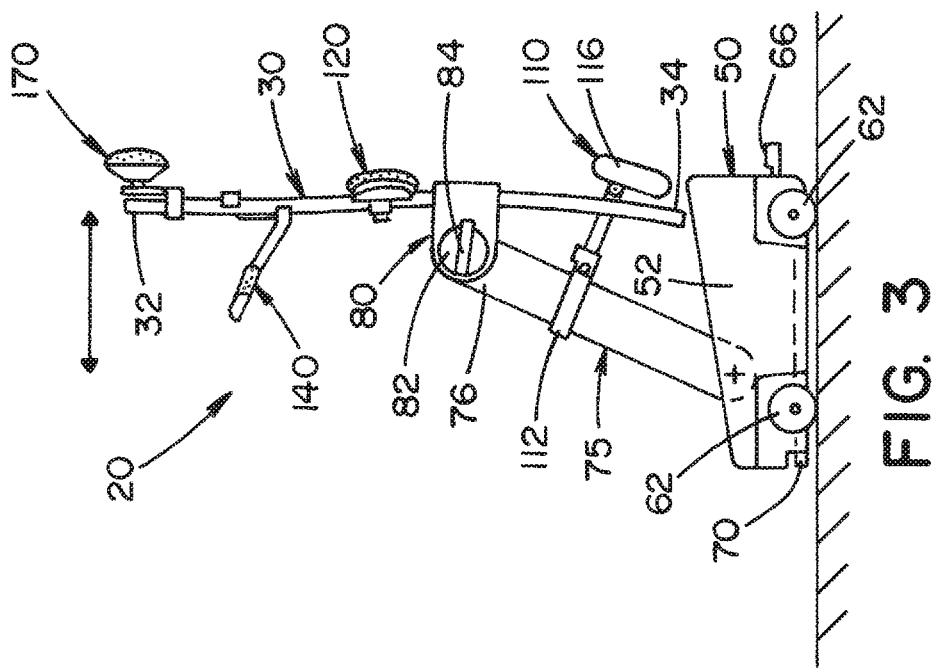

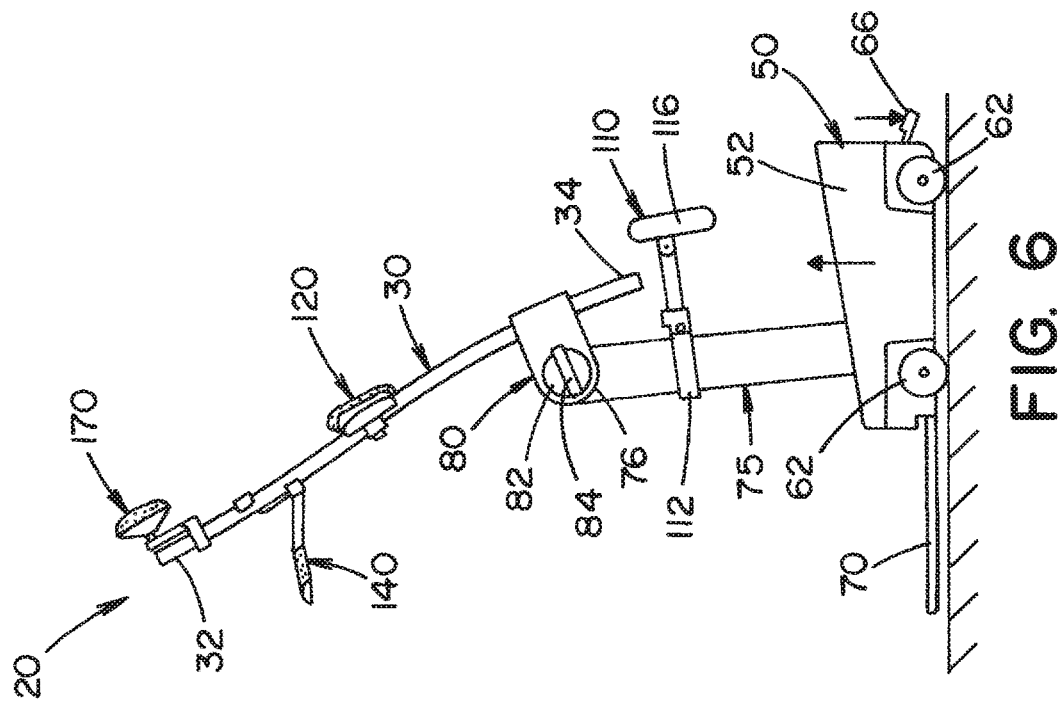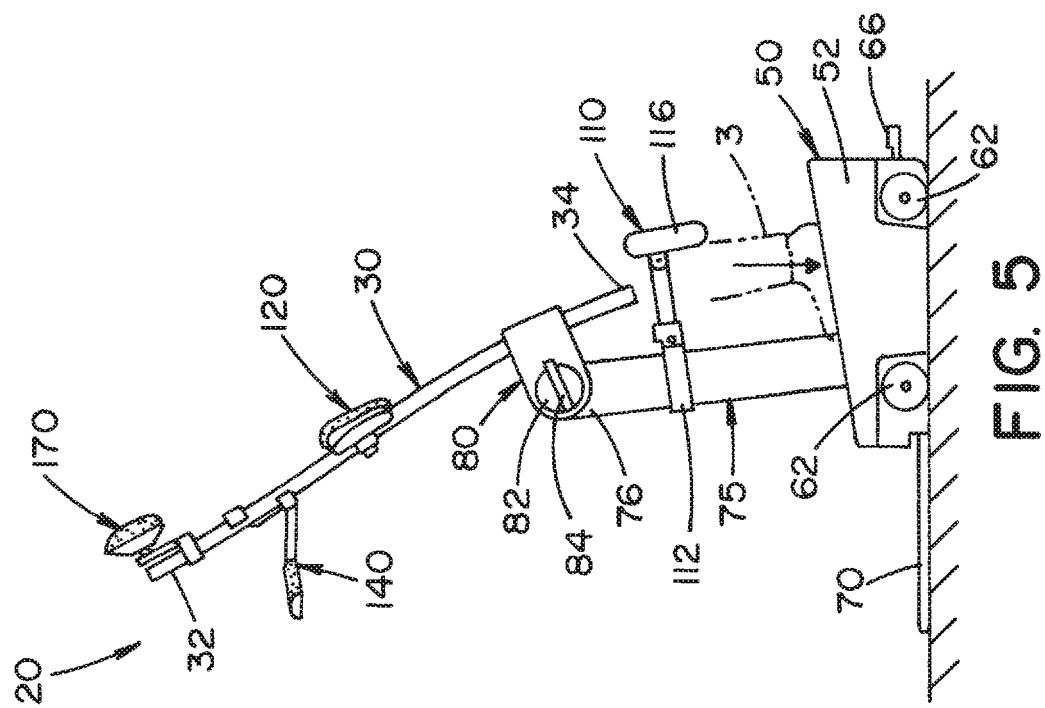

ERGONOMIC BODY POSITIONING SYSTEM

RELATED APPLICATIONS

This application claims the benefit of U.S. Provisional Application No. 62/489,156, filed Apr. 24, 2017, which is hereby fully incorporated herein by reference.

FIELD OF THE INVENTION

The present invention relates generally to a body support apparatus, and more particularly to an ergonomic body positioning system for use by surgeons while performing surgical procedures.

BACKGROUND OF THE INVENTION

Surgeons often operate in harsh and crowded environments with poor ergonomic posture for an extended period of time (e.g., 2-10 hours) thereby causing fatigue, repetitive motion injuries, and cumulative motion injuries that can shorten their surgical careers. A surgeon may develop a work related musculoskeletal disorder (MSD) due to maintaining awkward postures over these long hours. For example, a surgical operating table that is too low may lead a surgeon to bend the back and neck forward. On the other hand, a surgical operating table that is too high may lead to awkward positioning of the arms and shoulders. Frequent areas of concern are the back, wrists, neck, arms, shoulders, hamstrings, calves, and toes. Another common cause of MSD is standing upright for long time periods, which pools blood in the legs and feet, thereby causing aches and fatigue.

A study of these cumulative effects and their impact on surgical outcome has been referred to as "surgeon fatigue syndrome." These problems are magnified by many years of heavy workloads, with some surgeons performing numerous procedures (e.g., 15-20) each week. The prevalence of MSD disorders in surgeons has increased since 1995. A systematic review of work-related MSD disorders among surgeons and interventionists (https://www.ncbi.nlm.nih.gov/pubmed/29282463) concluded that degenerative cervical spine disease was present in 17% (457 of 2406 physicians), an increase in prevalence of 18.3% during the time period from 1995-2015. One contributing factor to this increase may be the need for both (1) wider surgical tables to perform certain types of surgical procedures (e.g., bariatric procedures) and (2) positioning methods for improved surgeon access to surgical sites. It can be difficult to satisfy both these needs, since a wider surgical table places a surgeon farther from the midline where the surgical sites are most likely to occur, thus impairing the surgeon's access to the surgical sites.

According to U.S. Department of Labor Occupation Safety and Health Administration (OSHA) publication 3125, "[a]dapting tasks, workstations, tools, and equipment to fit the user can help reduce physical stress on a user's body and eliminate many potentially serious, disabling work-related MSDs." In particular, OSHA recommends that "to minimize or prevent back disorders, employers should teach users to avoid long reaches [and] maintain neutral postures." A neutral posture is defined by Webster's New World Medical Dictionary as the stance that is attained "when the joints are not bent and the spine is aligned and not twisted." Another MSD risk factor described in OSHA 3125 is "awkward posture, or unsupported positions."

Ergonomics is defined by Merriam-Webster dictionary as "an applied science concerned with designing and arranging things people use so that the people and the things interact most efficiently and safely." In the field of ergonomics, the concept of the "postural triangle" indicates that a person's working posture is determined by three factors: (1) the task requirements, (2) the design of the workspace, and (3) personal factors such as body size and shape (Introduction to Ergonomics, Second Edition—Robert Bridger). An ergonomic positioning system should provide the ability for users of varying body sizes and shapes to readily adjust the workspace (positioning system) to meet the task requirements, while simultaneously maintaining good ergonomics including a neutral posture and full body support.

Several prior art apparatus have been developed to provide improved ergonomics for users, such as those disclosed in the following patent documents:

Apparatus to Assist a Mechanic to Work on a Vehicle (U.S. Pat. No. 6,957,718)
Multidirectional Personnel Lift (US 2006/0207021)
Operating Support for Surgeons (U.S. Pat. No. 3,754,787)
Operating Support for Surgeons (U.S. Pat. No. 8,480,168)
Surgeons Operating Chair (U.S. Pat. No. 3,029,106)
Leaning Device to Reduce Fatigue (U.S. Pat. No. 3,477,673)

However, it has been observed that these prior art apparatus do not simultaneously provide for improved surgical site access and elevation ("Up and Over"), while also placing a user (i.e., surgeon) in an ergonomically effective position (neutral posture) for performing surgery with support of the surgeon's chest, legs, and feet. If the chest is supported without ergonomic consideration of the lower body, then ergonomic injuries, discomfort, or fatigue may occur for the lower body.

Prior art apparatus do not ergonomically support the lower body to take force off of the legs, ergonomically support the upper body to take force off of the spine and arms, place the surgeon in a position that orients them in front of the surgical site without long reaches into the surgical space, and place the surgeon specifically so that their center of gravity is comfortably over the table with a neutral posture. Furthermore, prior art apparatus fail to support all of the surgeon's body weight for all of the limbs in a neutral posture, leading to less fatigue and less risk of MSD. Furthermore, the prior art fails to apply an overall systems approach to the above-described problems that incorporates the following elements: ergonomic surgeon positioning, improved surgical site access ("up and over"), unobtrusive support that does not obscure the operation table, flexible positioning and ease of adjustability for a wide range of male and female body types, convenient sterilization, and ergonomic accommodation of commonly used accessory items, such as lights and optics, a tool holder, and electrosurgical foot pedals.

In view of the foregoing, there is a need for an operating support apparatus for surgeons that addresses these and other drawbacks of prior art apparatus, improves the surgeon's access to the surgical site while maintaining ergonomics, and provides an overall systems approach.

SUMMARY OF THE INVENTION

In accordance with the present invention, there is provided a positioning system for supporting a body of a user proximate to a worksite, the positioning system comprising: a base; an arm mounted to the base; a stem mounted to the arm, wherein the stem is moveable relative to the base; and at least one support device for supporting the user's body, wherein the stem and the at least one support device substantially aligns the user's body along a neutral axis.

An advantage of the present invention is the provision of a body positioning system that provides improved ergonomic positioning and support of a user's body.

Another advantage of the present invention is the provision of a body positioning system that allows a user to maintain a neutral posture while accessing a worksite.

Another advantage of the present invention is the provision of a body positioning system that provides improved access to a worksite.

Another advantage of the present invention is the provision of a body positioning system that allows a user to have improved visibility into a worksite.

A still further advantage of the present invention is the provision of a body positioning system that locates the center of gravity of a user up and over a worksite.

A still further advantage of the present invention is the provision of a body positioning system that allows for user core alignment and less fatigue to the user.

A still further advantage of the present invention is the provision of a body positioning system that allows convenient adjustment to adapt to users of various body sizes and shapes.

A still further advantage of the present invention is the provision of a body positioning system having a small footprint.

A still further advantage of the present invention is the provision of a body positioning system that is simple and convenient to sterilize.

Yet another advantage of the present invention is the provision of a body positioning system that can accommodate commonly used accessory items, such as electrosurgical foot pedals, lighting devices, optical devices, and a tool holder.

Yet another advantage of the present invention is the provision of a body positioning system that provides a tool holder.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein:

FIG. 3 illustrates the body positioning system of FIG. 1 in a storage position;

FIG. 4 illustrates the body positioning system of FIG. 1 being configured into a use position;

FIG. 5 illustrates the body positioning system of FIG. 1 in the use position showing a user standing on a base of the system causing the wheels to lock;

FIG. 6 illustrates the body positioning system of FIG. 1 in the use position showing release of a foot pedal lever to unlock the wheels;

DETAILED DESCRIPTION OF THE INVENTION

Figure 1:
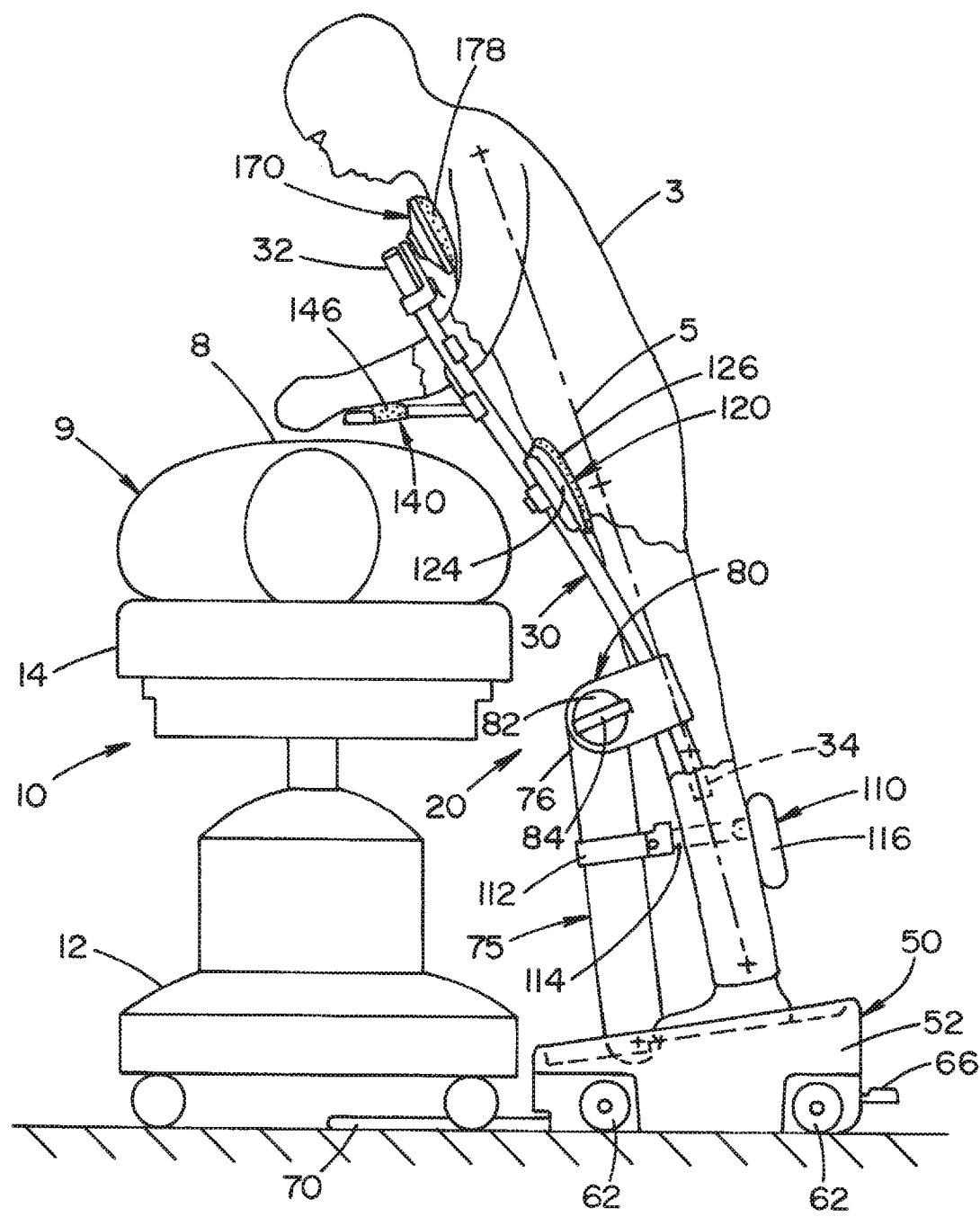
FIG. 1 illustrates a body positioning system according to an embodiment of the present invention, said body positioning system shown as used by a surgeon to access a patient's body during a surgical procedure.

Referring now to the drawings wherein the showings are for the purposes of illustrating embodiments of the invention only and not for the purposes of limiting same, FIG. 1 shows a body positioning system 20 according to an embodiment of the present invention. System 20 supports and positions a user 3 relative to a worksite 8. In the illustrated embodiment, user 3 is a surgeon (or a surgical staff member) and worksite 8 is a surgical site of a patient 9. Patient 9 is supported by a surgical table 10 having a base 12 and a height-adjustable patient support 14.

System 20 allows a user to maintain a neutral posture while accessing worksite 8. In this regard, user 3 maintains a neutral body position along a substantially linear neutral axis 5, as shown in FIG. 1. Neutral posture allows for core alignment and less fatigue. System 20 supports and positions user 3 such that user 3 has an unobstructed view into worksite 8. In this regard, user 3 is positioned up and over patient 9, thereby improving visibility into worksite 8. Furthermore, the center of gravity of user 3 is up and over patient 9 and table 10.

System 20 supports a user's overall posture for both upper and lower body (e.g., head, chin, chest, forearm, hamstring, shin, and feet), and allows convenient adjustments to adapt system 20 to support various body sizes and shapes. System 20 is especially useful during long surgical procedures, to access larger patients, and to provide improved positioning for shorter users relative to the worksite.

Figure 2:
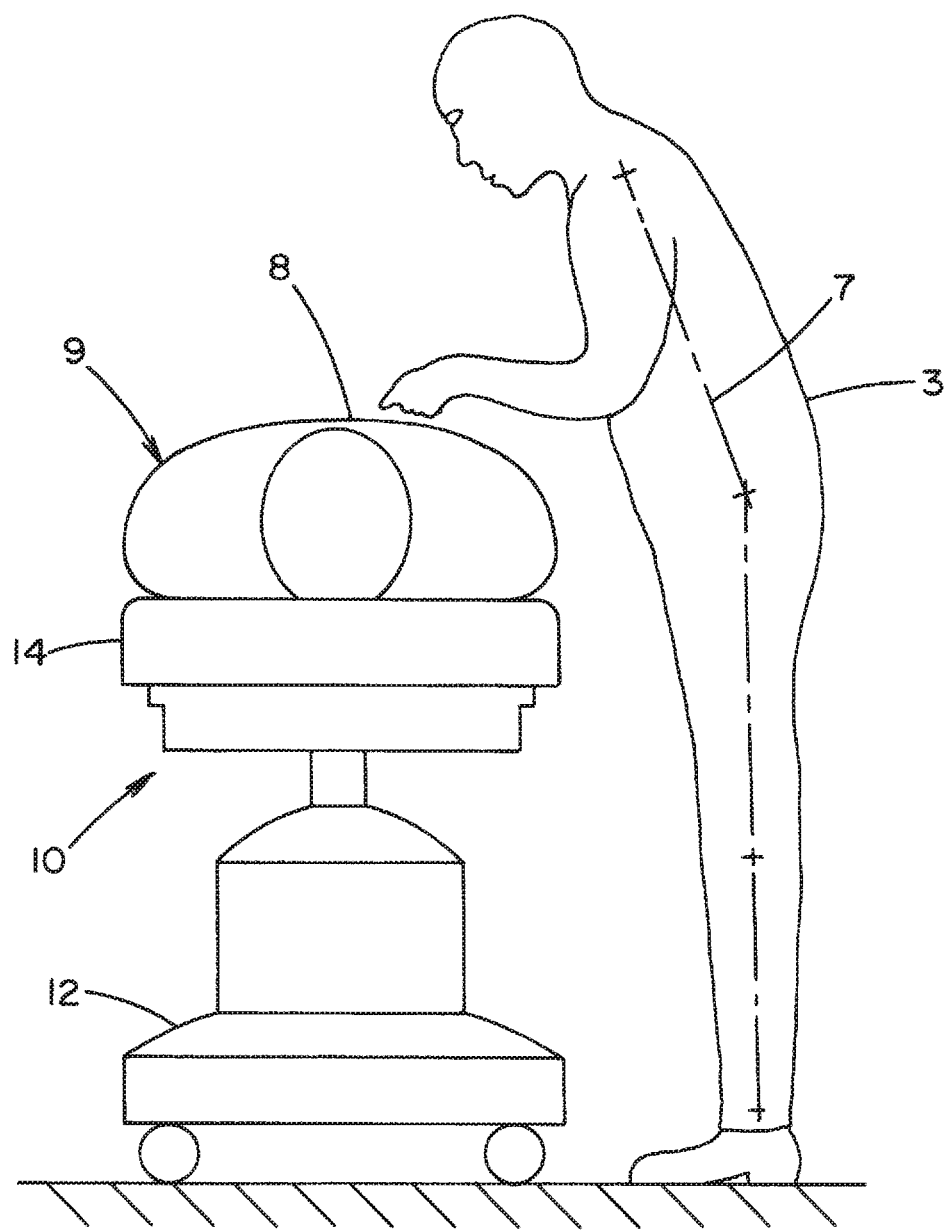
FIG. 2 shows the body position of a surgeon while conducting a surgical procedure on a patient's body in a conventional manner without use of a body positioning system.

FIG. 2 shows a user 3 with typical access to a worksite 8 without use of system 20. As illustrated, the body position of user 3 is maintained along a non-linear axis 7, and thus, user 3 does not maintain a neutral posture while accessing worksite 8. Furthermore, with typical access to worksite 8, user 3 is not positioned up and over patient 9, and thus, has poorer visibility into worksite 8.

System 20 is generally comprised of a stem 30, a base 50, a rotatable support arm 75, an adjustment member 80, and a plurality of support devices that are described in detail below.

Stem 30 serves as the main load-carrying member of system 20. As best seen in FIGS. 1, 3-6, 11A-11B, 12A-12B, and 13-14, stem 30 is a tubular member having an upper portion 32 and a lower portion 34. A plurality of recesses 36 are formed along the length of stem 30 that function as indexing members for attachment of support devices. Additional indexing members (e.g., grooves or teeth) may be formed along a portion of stem 30 to facilitate height adjustment of stem 30, as will be explained below.

In the illustrated embodiment, stem 30 has an S-shaped curvature and an elliptical cross-section. Upper portion 32 recurves toward the user allowing the user to keep their posture upright, while bottom portion 34 recurves away from the user allowing for stem 30 to rotate the user up and over the worksite as the height of stem 30 is extended. In one embodiment of the present invention, stiffening ribs (not shown) are provided on the interior of stem 30 to counter bending moments from a user's weight. In the illustrated embodiment stem 30 is made of a lightweight but strong material, such as aluminum, carbon fiber, titanium, and the like. To preserve strength, an annealing process may be used to harden the material.

It should be appreciated that stem 30 has a profile to accommodate a user's close proximity to the worksite but still be supportive and "stiff" to provide the user with confidence in the support provided by stem 30. It is contemplated that stem 30 may be constructed using a floating mandrel extruding technology. The S-shaped curvature of stem 30 may be formed by a tube bending processes common in industries such as aerospace. Recesses 36 may be roll-formed tube stamped or machined.

Figure 7:
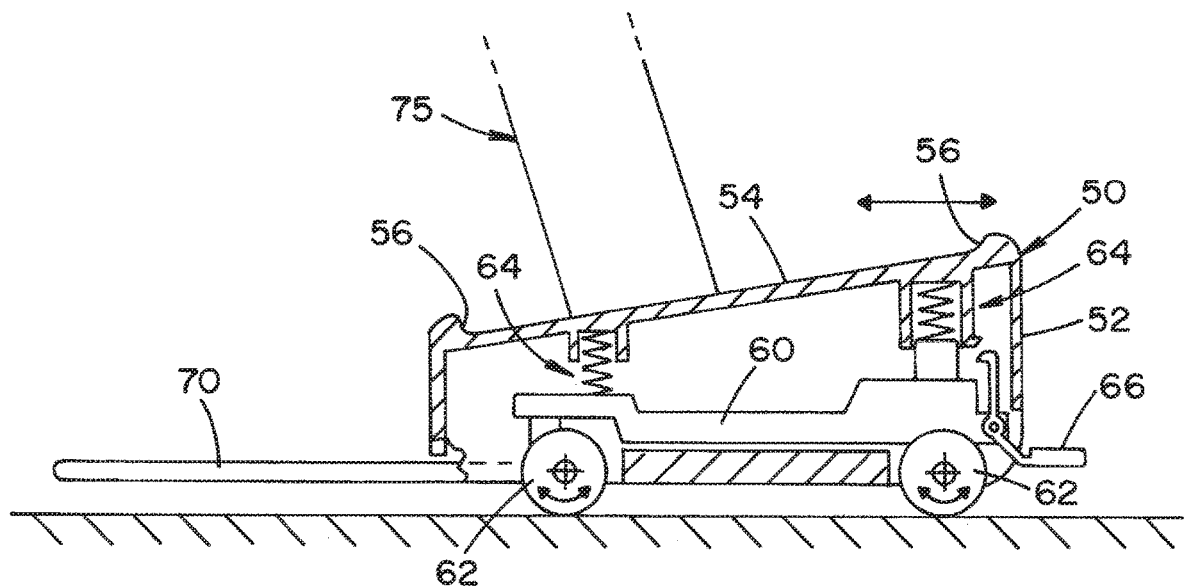
FIG. 7 illustrates a cross-sectional view of the base showing the wheels in an unlocked position before a user stands on the base.
Figure 8:
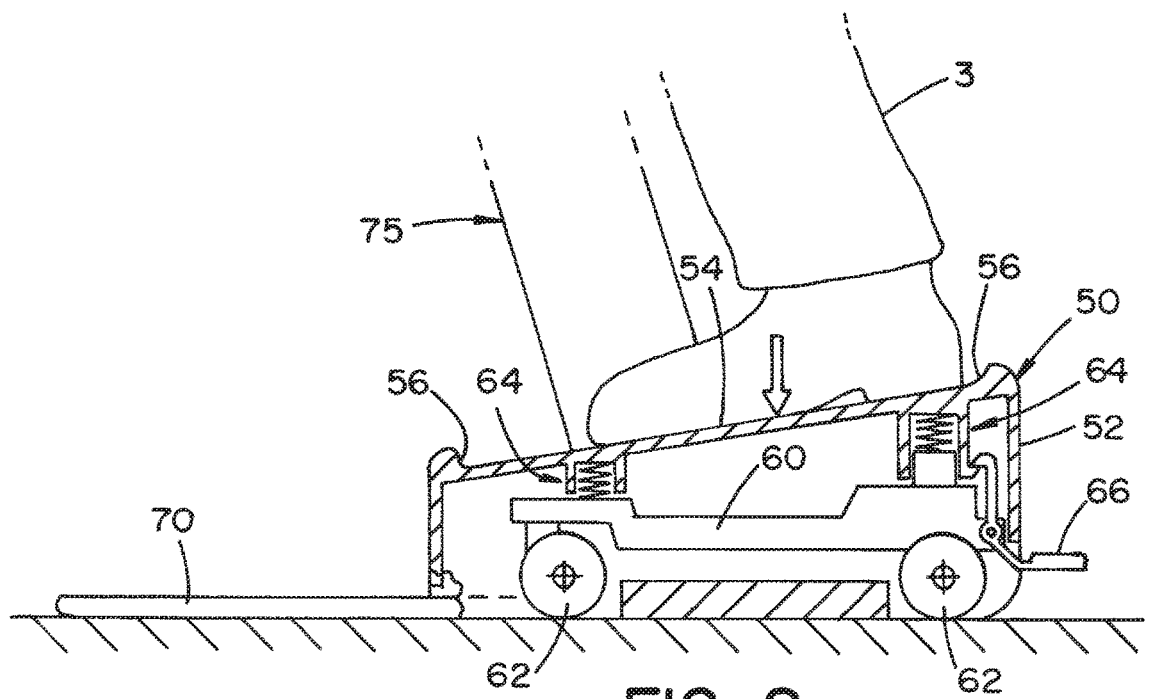
FIG. 8 illustrates a cross-sectional view of the base of the system showing the wheels in a locked position with a user standing on the base.
Figure 9:
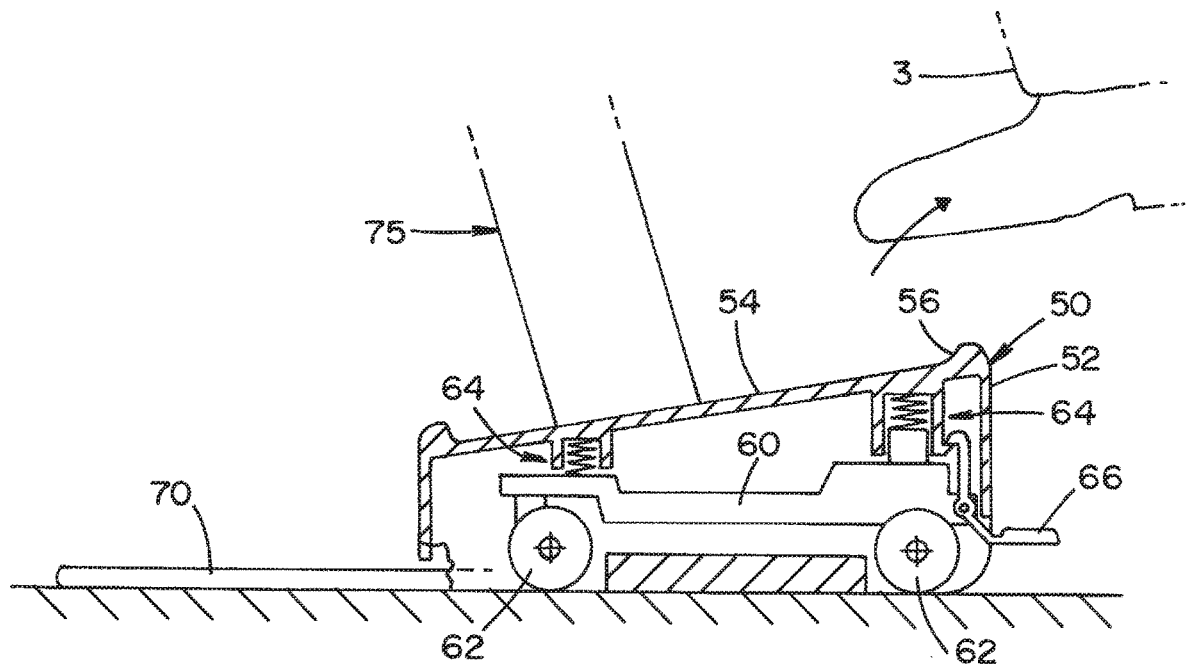
FIG. 9 illustrates a cross-sectional view of the base showing the wheels in the locked position after a user steps off the base.
Figure 10:
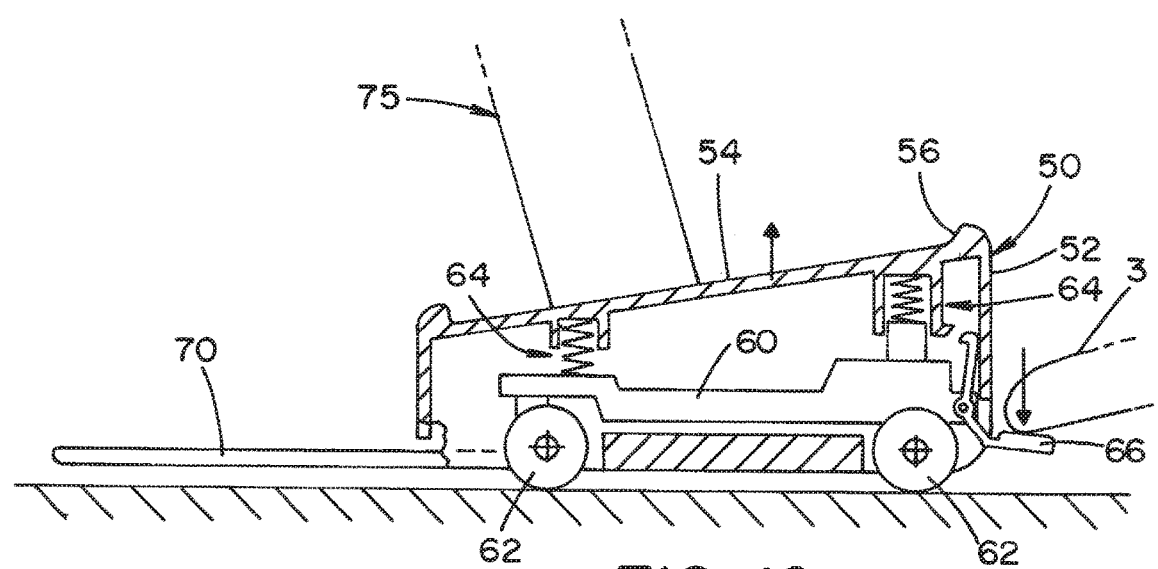
FIG. 10 illustrates a cross-sectional view of the base showing the wheels in the unlocked position due to release of the foot pedal lever.
Figure 11A:
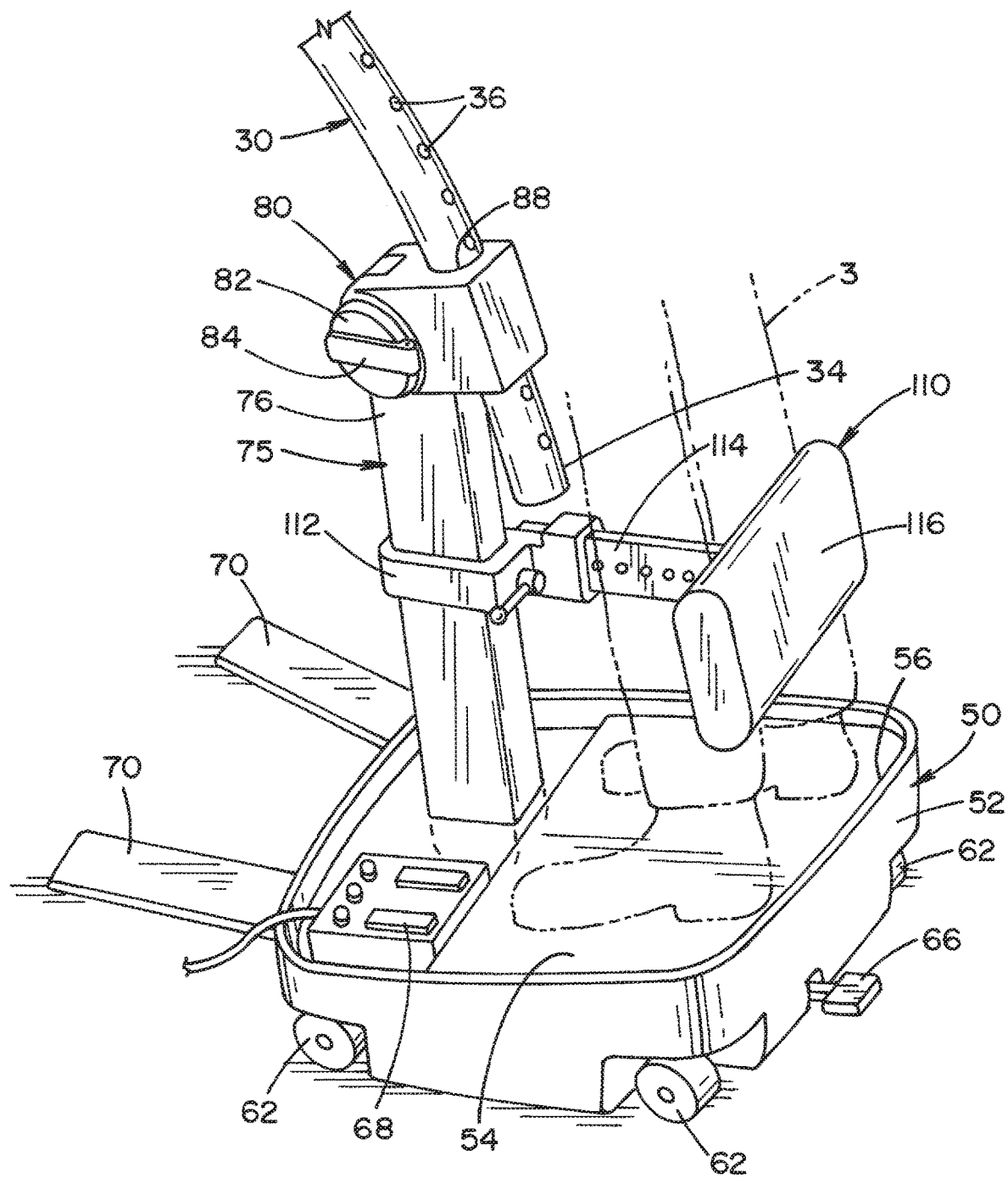
FIG. 11A illustrates a perspective view of a lower portion of the body positioning system showing a calf support according to an embodiment of the present invention.
Figure 11B:
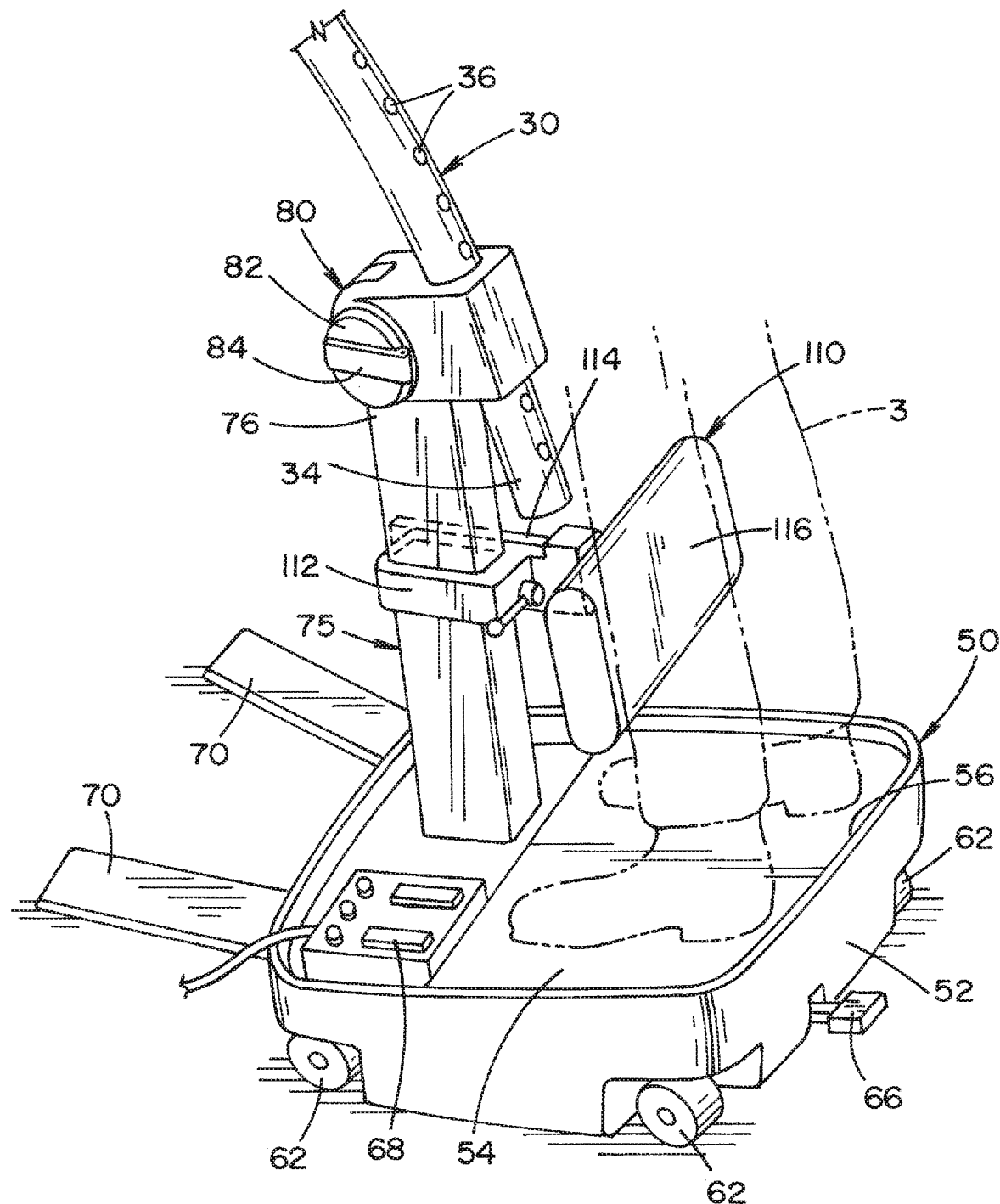
FIG. 11B illustrates a perspective view of a lower portion of the body positioning system showing a shin support according to an embodiment of the present invention.

Base 50 will now be described in detail with reference to FIGS. 7-10, 11A, and 11B. Base 50 is generally comprised of a cover or housing 52, and a platform or chassis 60. In the illustrated embodiment, housing 52 has a sloping top wall 54 and a peripheral heel lip 56. In the illustrated embodiment of the present invention, the slope angle of top wall 54 is in a range of 8-20 degrees from a horizontal line of the ground surface. Heel lip 56 provides support to the user's foot. A plurality of caster wheels 62 are mounted to chassis 60. Wheels 62 allows system 20 to be conveniently moved to a desired location proximate to a worksite. In an illustrated embodiment, wheels 62 are approximately 2 inches in diameter to allow for a roll center of 1 inch for obstacle clearance. Housing 52 is mounted to the upper surface of chassis 60 by spring-loaded mounts 64, as seen in FIGS. 7-10. A conventional braking system (not shown) is engaged by downward movement of housing 52 to lock wheels 62. A foot pedal lever 66 is mounted to chassis 60 and is rotatable for engagement with a flange or lip of spring-loaded mount 64. Wheels 62 remain locked by the braking system when lever 66 is engaged with the flange or lip of spring-loaded mount 64. In FIGS. 7 and 10 the braking system is disengaged, and thus, wheels 62 are unlocked. In FIGS. 8 and 9 the braking system is engaged, and thus, wheels 62 are locked. Base 50 also includes a conventional gearing arrangement (not shown) that operatively connects the lower end of rotatable support arm 75 with stabilizer forks 70, which are best seen in FIGS. 11A and 11B. Forks 70 are moveable between an extended position and a retracted position by rotation of support arm 75.

It should be appreciated that in accordance with one embodiment of the present invention, the braking system is comprised of a lower surface of housing 52 that engages with an upper surface of wheels 62 in response to downward movement of housing 52. In another embodiment of the present invention, the braking system is comprised of housing 52 that engages with the floor as a result of downward movement of housing 52. This engagement with the floor makes wheels 62 inactive.

A control pedal 68 and anti-fatigue mat (not shown) may be accommodated on top wall 54. Control pedal 68 may take the form of electrosurgical foot pedal (e.g., electrocautery pedal). A recess (e.g., ½-¾ inch) may be formed in top wall 54, approximately 10-14 inches from heel lip 56, to receive control pedal 68. The anti-fatigue mat may be formed of polyurethane and have a thickness in the range of ¼-1 inch. In one embodiment of the present invention, the anti-fatigue mat may include a "low friction" surface located at a region of the mat where a user's heal contacts the anti-fatigue mat. This low friction surface allows for the rotation of the user's foot without placing torsional loading at the knee joint.

Rotatable support arm 75 has an upper end 76 that is connected with adjustment member 80 and a lower end that connects with the gearing arrangement housed in base 50. Support arm 75 is best seen in FIGS. 3-6, 11A and 11B. Support arm 75 moves between a storage position (FIG. 3) and a use position (FIG. 5). FIG. 4 shows support arm 75 in an intermediate position. In the storage position, forks 70 are retracted inside housing 52 for convenient compact storage of system 20. In the use position, forks 70 extend outward from housing 52 to provide stabilizing support for system 20.

Figure 14:
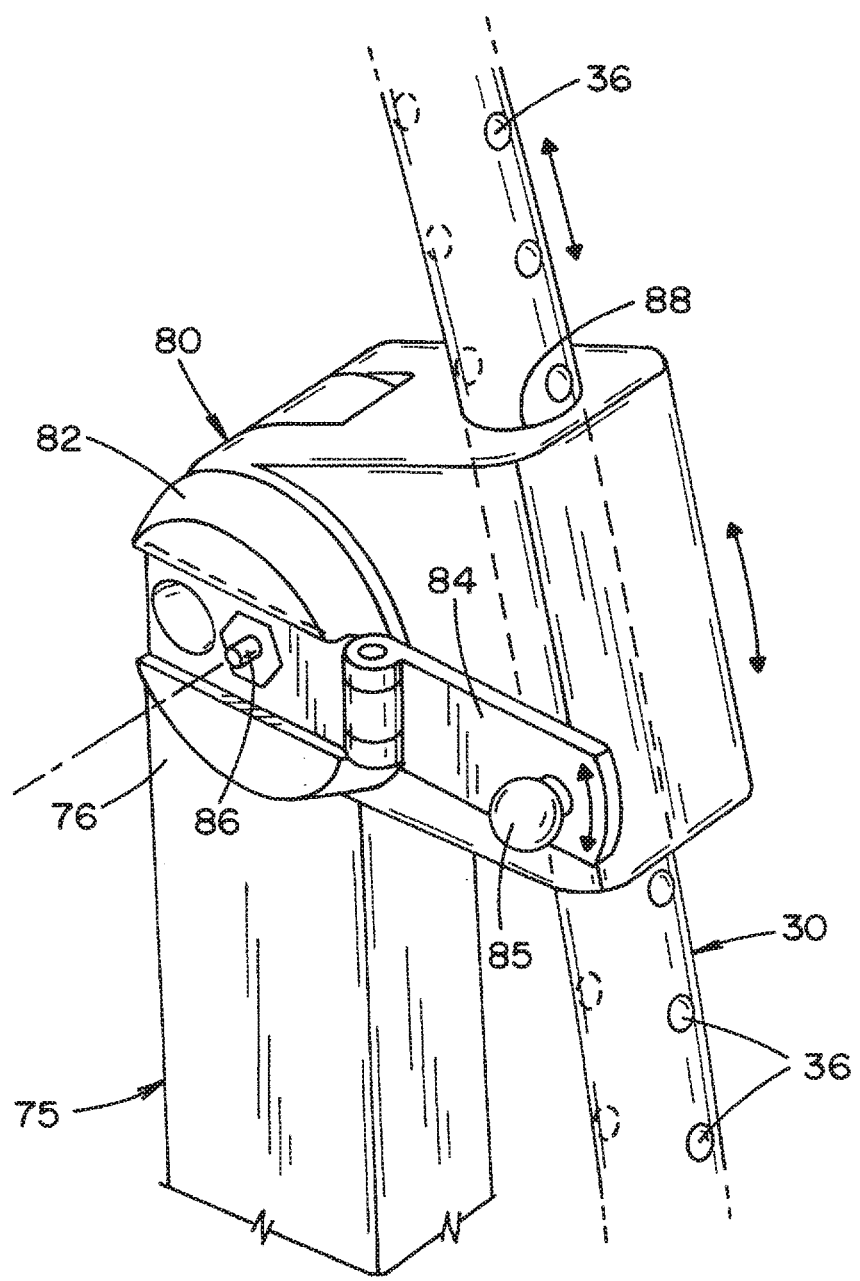
FIG. 14 illustrates a perspective view of an adjustable member according to an embodiment of the present invention, said adjustable member in an unlocked position.

As best seen in FIGS. 4, 11A, 11B, 13 and 14, adjustment member 80 is rotatable about an axis generally transverse to the longitudinal axis of arm 75. Rotation of adjustment member 80 adjusts the angle (pitch) of stem 30. Adjustment member 80 includes a channel 88 dimensioned to receive a section of stem 30, a rotatable disk 82, a hinged lever 84 mounted to disk 82, and a locking pin 86. Lever 84 includes a knob 85 to facilitate rotation of disk 82. Adjustable member 80 also includes a conventional gearing arrangement (not shown) for interconnecting adjustment member 80 with stem 30. For example, a plurality of gear teeth may engage with grooves, or other indexing members, located along a length of stem 30. The gearing arrangement is activated by rotation of disk 82 using knob 85. Rotation of disk 82 provides for height adjustment of stem 30 (FIG. 14). When locking pin 86 is engaged by moving lever 84 to a closed position (FIG. 13), rotation of adjustment member 80 is prevented and the gearing arrangement is locked to prevent further adjustment. Adjustment member 80 provides means for adjusting both the pitch and height for stem 30 to accommodate users of various sizes and shapes.

Support devices according to an embodiment of the present invention will now be described with reference to FIGS. 11A-11B, 12A-12B, 15-18, and 20-22.

FIGS. 11A and 11B show a lower leg support 110 that can function as a calf support (FIG. 11A) or a shin support (FIG. 11B). Lower leg support 110 is comprised of an engagement member 112 for attachment to support arm 75, a mounting bracket 114 for horizontal adjustment of lower leg support 110, and a pad 116. Pad 116 may be comprised of a support base and foam.

Figure 12A:
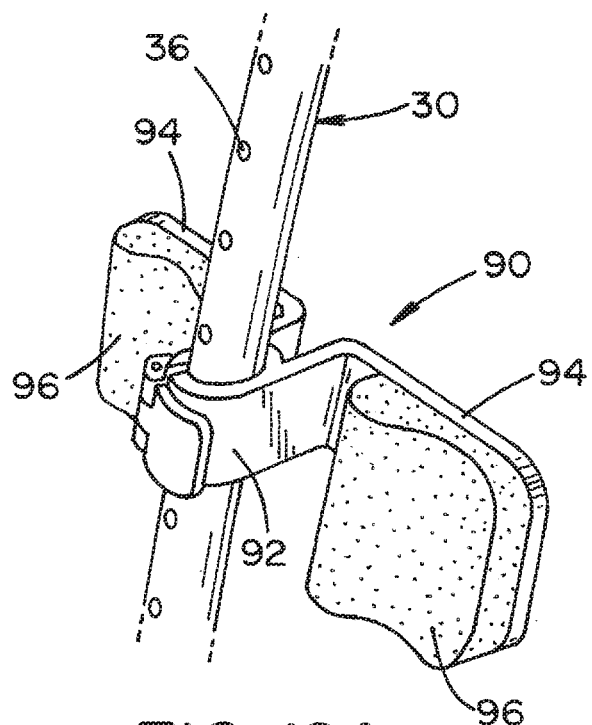
FIG. 12A illustrates a perspective view of a lower portion of the body positioning system showing a shin support according to another alternative embodiment of the present invention.

FIG. 12A illustrates an alternative lower leg support 90 that functions as a shin support. Lower leg support 90 is comprised of an engagement member 92 for attaching lower leg support 90 to stem 30, a pair of arms 94, and pads 96. In the illustrated embodiment, engagement member 92 takes the form of a locking clamp. Furthermore, in the illustrated embodiment, arms 94 are formed of a plastic material or a sterilize-able stainless-steel material.

Figure 12B:
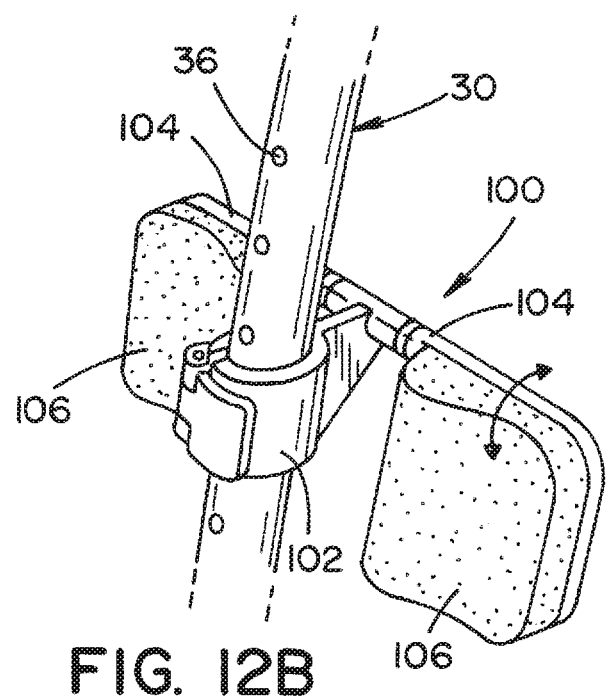
FIG. 12B illustrates a perspective view of a lower portion of the body positioning system showing a shin support according to yet another alternative embodiment of the present invention.
Figure 13:
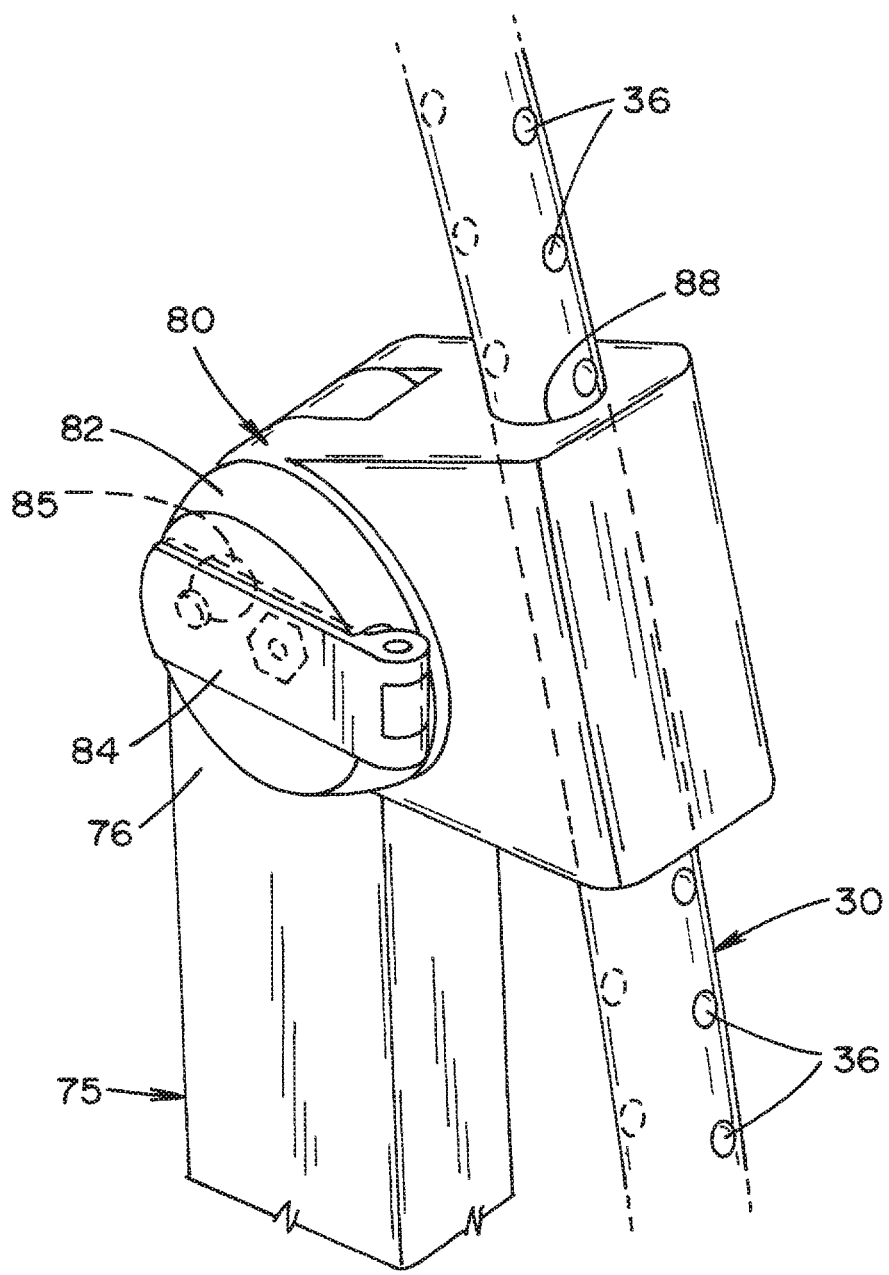
FIG. 13 illustrates a perspective view of an adjustable member according to an embodiment of the present invention, said adjustable member in a locked position.

FIG. 12B illustrates another alternative lower leg support 100 that functions as a shin support. Lower leg support 100 is comprised of an engagement member 102 for attaching lower leg support 100 to stem 30, a pair of spring-loaded rotatable arms 104, and pads 106. In the illustrated embodiment, engagement member 102 takes the form of a locking clamp. Furthermore, in the illustrated embodiment, arms 104 are formed of a plastic material or a sterilize-able stainless-steel material.

Figure 15:
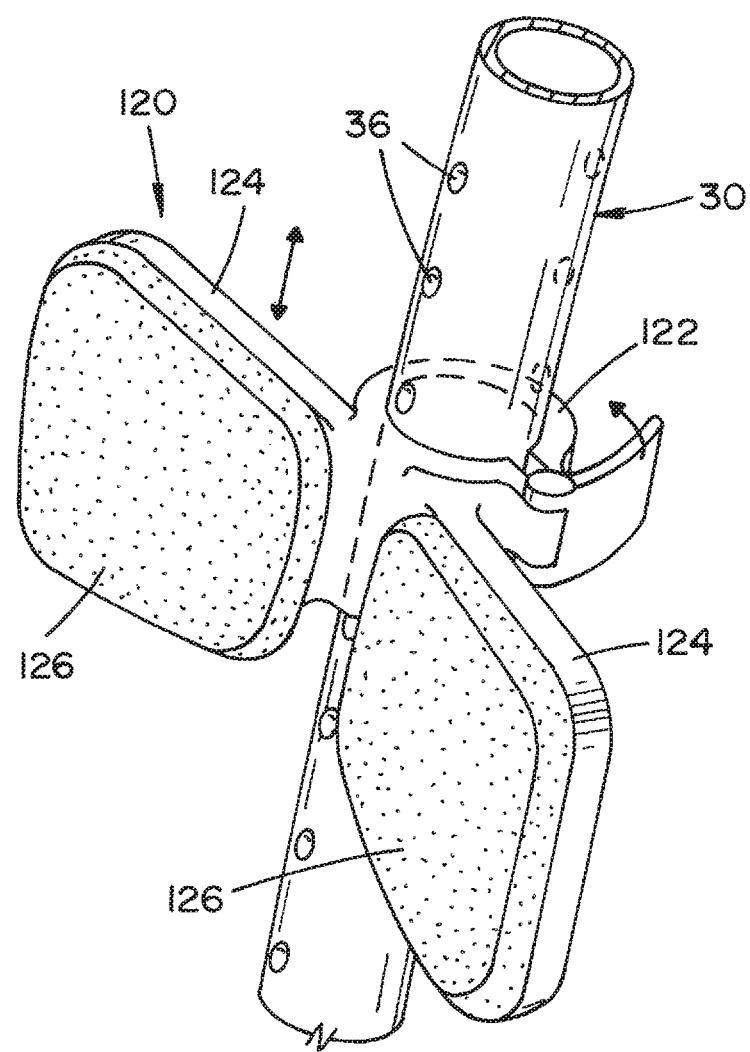
FIG. 15 illustrates a perspective view of a waist support according to an embodiment of the present invention.

Referring now to FIG. 15, there is shown a waist support 120. Waist support 120 is comprised of an engagement member 122 for attaching waist support 120 to stem 30, a pair of arms 124, and pads 126. In the illustrated embodiment, engagement member 122 takes the form of a locking clamp. Arms 124 may be formed of a rigid material, such as a plastic material or a sterilize-able stainless-steel material.

Figure 16:
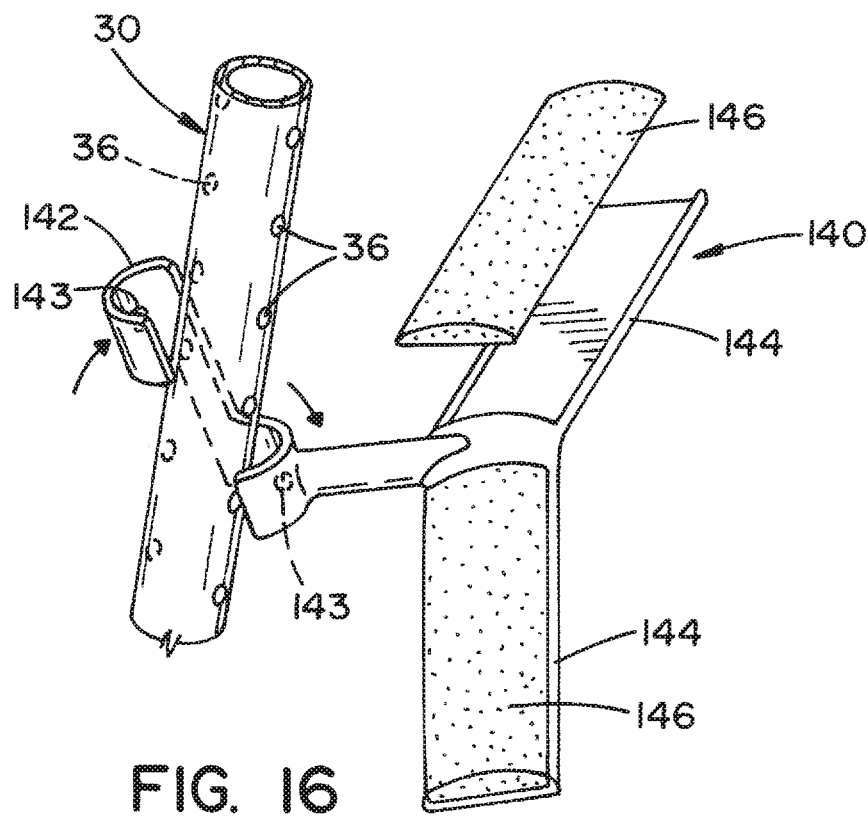
FIG. 16 is an exploded perspective view of an elbow/forearm support according to an embodiment of the present invention.
Figure 17:
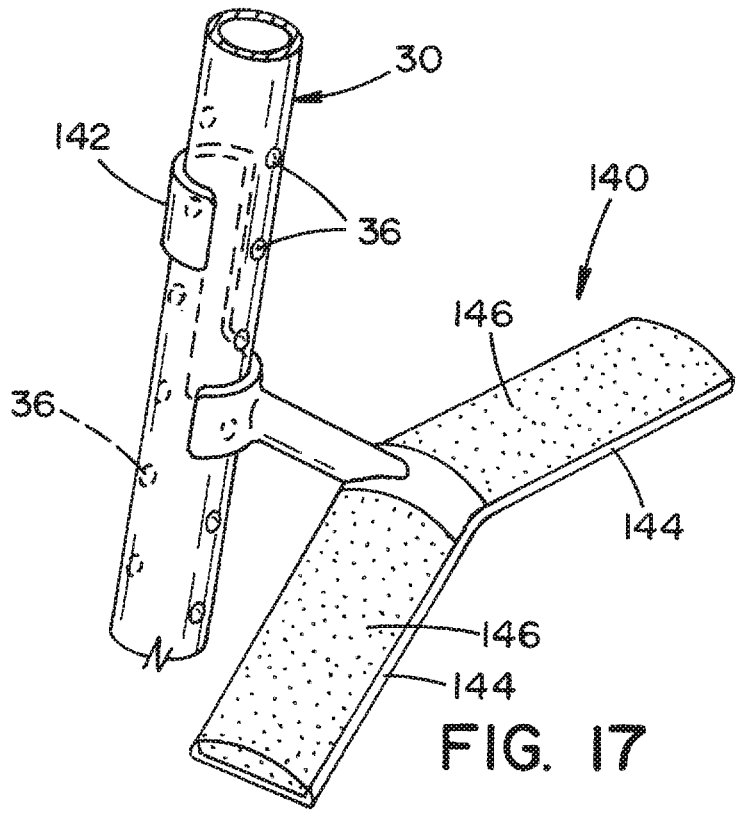
FIG. 17 is a perspective view of the elbow/forearm support shown in FIG. 16, said elbow/forearm mounted to a stem of the system.
Figure 18:
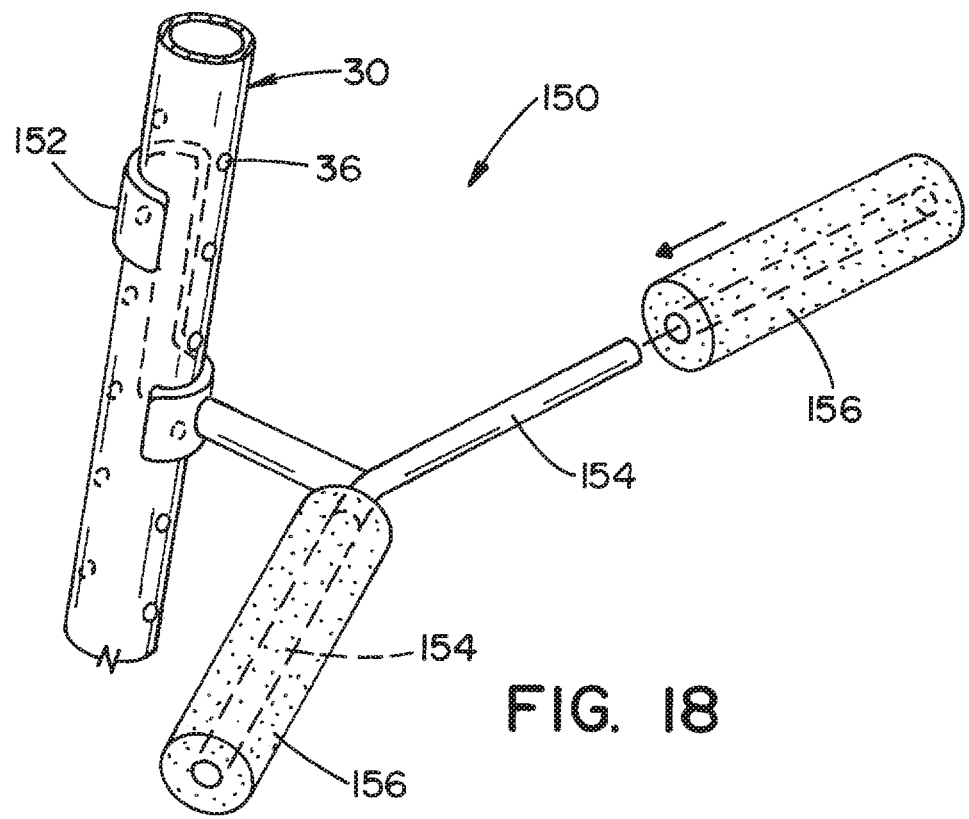
FIG. 18 is an exploded perspective view of an elbow/forearm support according to another embodiment of the present invention.

FIGS. 16 and 17 show an elbow/forearm support 140 according to an embodiment of the present invention. Elbow/forearm support 140 allows a user to steady his/her hand at the worksite. Elbow/forearm support 140 comprises an engagement member 142 that attaches elbow/forearm support 140 to stem 30, a pair of arms 144, and pads 146. In the illustrated embodiment, engagement member 142 includes pins 143, which are dimensioned to be received into recesses 36 of stem 30. FIG. 17 shows elbow/forearm support 140 attach to stem 30. FIG. 18 shows an alternative elbow/forearm support 150. Elbow/forearm support 150 comprises an engagement member 152, a pair of arms 154, and pads 156. Elbow/forearm support 150 attaches to stem 30 in the same manner as elbow/form support 140 described above. In the illustrated embodiments, arms 144 and 154 are formed of a plastic material or a sterilize-able stainless-steel material.

Figure 20:
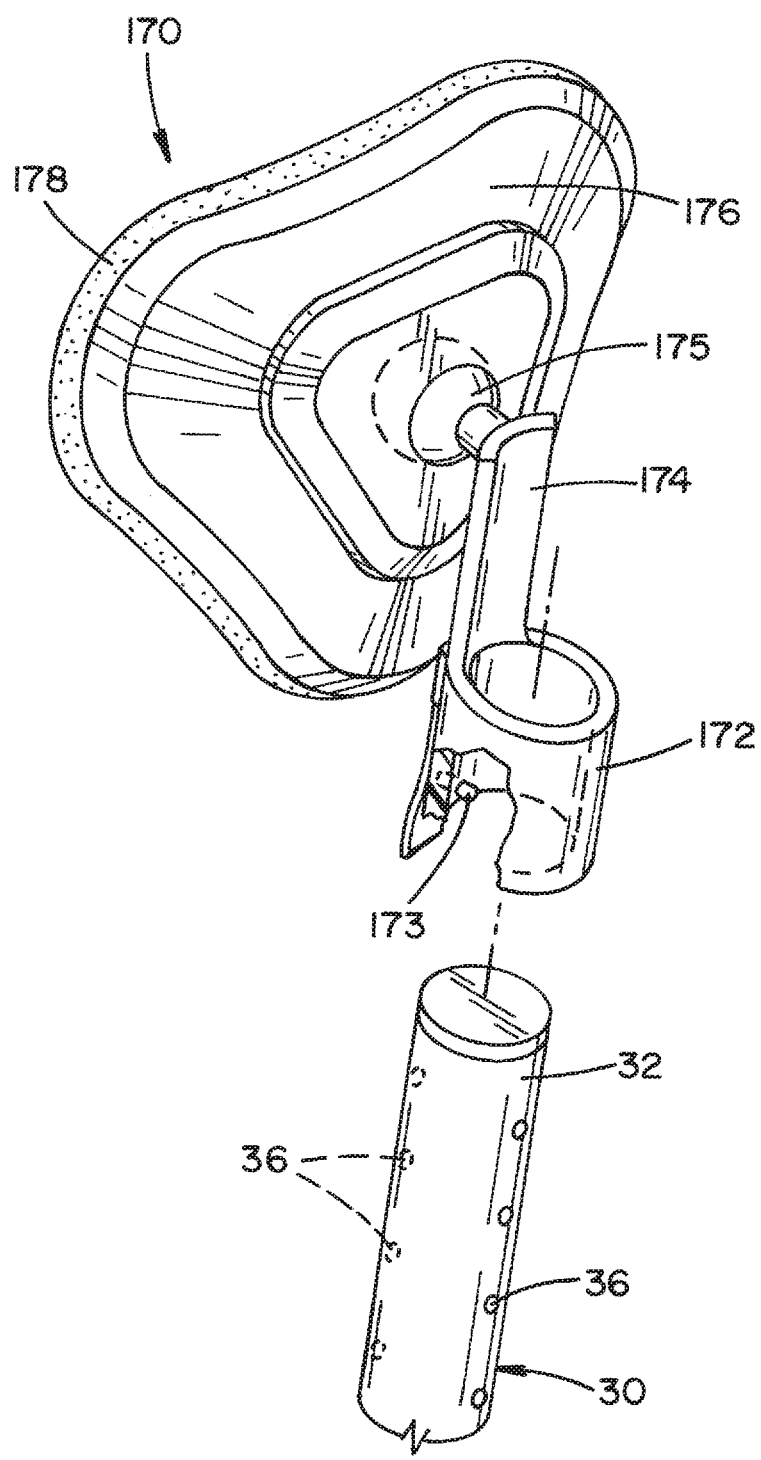
FIG. 20 is a partial cutaway perspective view of a chest support according to an embodiment of the present invention.
Figure 21:
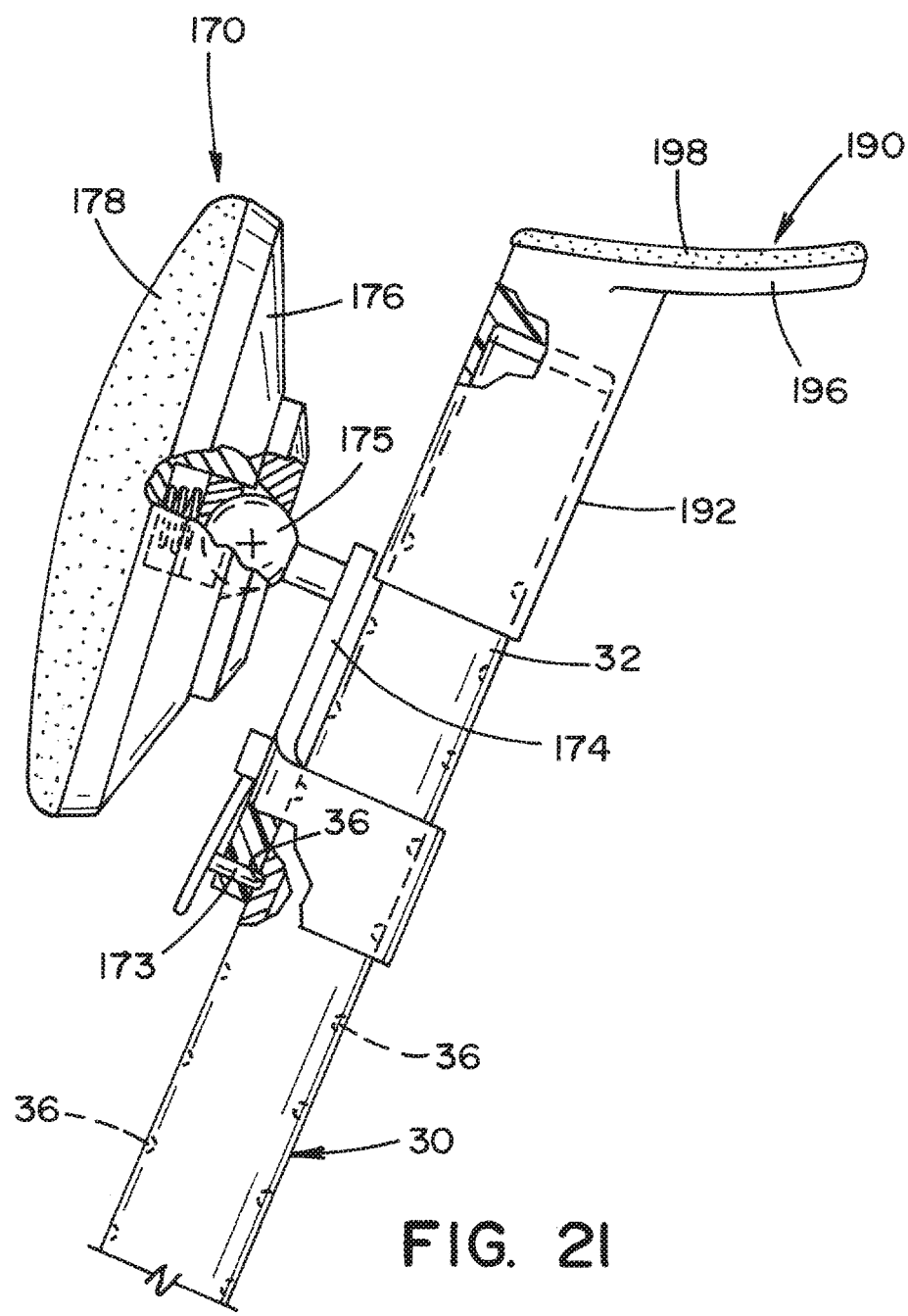
FIG. 21 is a partial sectional perspective view of the chest support shown in FIG. 20, the chest support mounted to the stem.

FIG. 20 shows a chest support 170 according to an embodiment of the present invention. Chest support 170 comprises a cylindrical engagement member 172 for mounting chest support 170 to stem 30, an arm 174 having a spring-loaded ball joint 175, a support base 176, and a pad 178. Engagement member 172 includes a spring-loaded locking pin 173 dimensioned to be received in recesses 36 of stem 30 to fix chest support 170 to stem 30. Support base 176 is mounted to arm 174 via ball joint 175. Ball joint 175 allows for rotation of a user's upper body. A partial cross-sectional view of chest support 170 is shown in FIG. 21. In the illustrated embodiment, support base 176 is formed of a plastic material or a sterilize-able stainless-steel material.

The load-carrying member for the surgeon's upper body while mounted on system 20 is the chest support. Due to anatomy considerations, the chest support is detachable and can have pads of various dimensions adapted for both men and women of different sizes and shapes.

Figure 22:
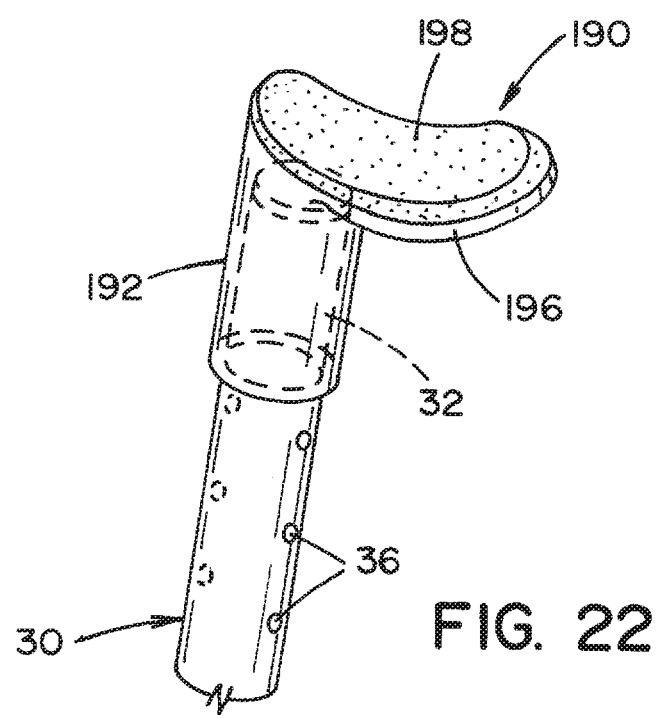
FIG. 22 is a perspective view of a chin support according to an embodiment of the present invention, the chin support mounted to the stem.

FIGS. 21 and 22 show a chin support 190 according to an embodiment of the present invention. Chin support 190 comprises a cylindrical engagement member 192 for mounting chin support 190 to the distal end of stem 30, a support base 196, and a pad 198. In the illustrated embodiment, support base 196 is formed of a plastic material or a sterilize-able stainless-steel material. Chin support 190 allows a user to decrease strain on his/her neck while allowing freedom of motion of the head and neck when needed by lifting off of chin support 190. Chin support 190 slides up and down with a slight interference fit on the top of stem 30 allowing for a 1-3 inch stand off from the top end of stem 30.

The pads for the support devices described above may be comprised of a foam core and a fabric cover. For example, the foam core may include a 2-layer foam comprising a memory foam immersive layer (⅛-½" softcore memory foam, 4.0 lb. density) and a stiffer foam layer (⅛-½" 1840-1850 hr polyurethane foam) to bolster the memory foam immersive layer. The fabric cover may take the form of a 4-way stretch polyurethane fabric.

It is contemplated that system 20 may include support devices other than those illustrated herein. For example, system 20 may also include a hamstring support that attaches to stem 30 or arm 75 in a similar manner as the lower leg supports that are described above.

Figure 19:
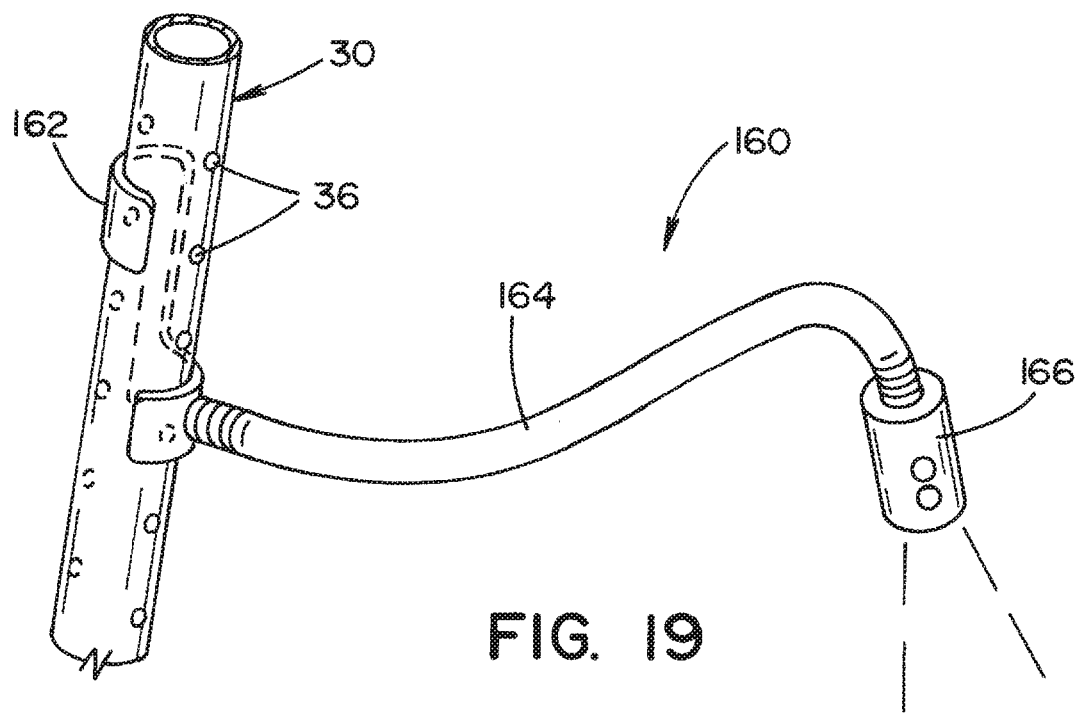
FIG. 19 is a perspective view of an accessory device according to an embodiment of the present invention, as mounted to the stem.

FIG. 19 illustrates an exemplary accessory device that may also be attached to stem 30. In the illustrated embodiment, accessory device 160 takes the form of an adjustable lighting device that includes an engagement member 162 (which is substantially the same as engagement members 142, 152 described above) that is mountable to stem 30, a flexible arm 164, and a battery-powered LED lighting unit 166 located at the distal end of flexible arm 164. Lighting unit 166 can be used to shine light directly into the worksite. Accordingly, lighting unit 166 can eliminate the need for a headlamp light mounted to a user's head, thereby reducing neck strain. It is contemplated that the accessory device may take various alternative forms, including, but not limited to, a perch, a tool rest, a storage tray, a camera, an optical magnifying device, a fiber optic light pipe, and a mounting for a retractor.

It should be appreciated that the support and accessory devices described above may be disposable or sterilizable.

Body positioning system 20 may also include a disposable sterile cover (not shown) to encapsulate the components described above. The cover may be made of common plastic sterile draping materials, such as thermoplastic materials which can be RF, impact, or ultrasonically welded. Ties are affixed via this welding process or bonded to allow the sterile cover to be conformal to system 20 and not drape onto a surgical field.

Basic operation of system 20 will now be described with reference to FIGS. 3-10. In FIG. 3, system 20 is shown as configured for transport and storage, with support arm 75 in the storage position (rotated inward) and stabilizer forks 70 retracted. FIG. 4 shows support arm 75 in an intermediate position as it is moved from the storage position to the use position. In FIGS. 5 and 7, system 20 is shown as configured in position for use with support arm 75 in the use position (rotated outward) and stabilizer forks 70 extended. In FIG. 8, system 20 is shown in use with a user standing on base 50. When a user steps onto base 50 applying weight thereto, the springs of spring-loaded mounts 64 compress as housing 52 moves toward the floor. This action causes engagement of the braking system and activation of foot pedal lever 66 to engage with the flange of spring-loaded mount 64. As a result, wheels 62 are locked. FIGS. 6 and 9 show system 20 when a user steps off base 50, thereby removing weight therefrom. Wheels 62 remain locked until foot pedal lever 66 is depressed to release the flange of spring-loaded mount 64, as shown in FIG. 10. The release of the flange of spring-loaded mount 64 allows housing 52 to move away from the floor, thereby disengaging the braking system that locks wheels 62.

The foregoing describes specific embodiments of the present invention. It should be appreciated that these embodiments are described for purposes of illustration only, and that numerous alterations and modifications may be practiced by those skilled in the art without departing from the spirit and scope of the invention. For example, it is contemplated that the present invention may be adapted for other applications that involve working for extended periods of time in a standing position over a workspace that is removed from the body. Such applications include, but are not limited to, auto repair, line assembly work in a manufacturing plant, and home chores, such as dishwashing. It is intended that all such modifications and alterations be included insofar as they come within the scope of the invention as claimed or the equivalents thereof.

Having described the invention, the following is claimed:

1. A positioning system for supporting a body of a user proximate to a worksite, the positioning system comprising:
    a base, comprising:
        a chassis having a plurality of wheels; and
        a housing that covers the chassis;
    an arm mounted to the base;
    a stem mounted to the arm, the stem being moveable relative to the base; and
    at least one support device for supporting the body of the user,
    wherein the stem and the at least one support device substantially aligns the body of the user along a neutral axis, and
    wherein said housing is mounted to the chassis by spring-loaded mounts for engagement of a braking system to lock the wheels.

2. The positioning system according to claim 1, wherein the stem has an S-shaped curvature.

3. The positioning system according to claim 1, wherein the base further comprises:
    a foot pedal lever for disengagement of the braking system to unlock the wheels.

4. The positioning system according to claim 1, wherein the at least one support device is mounted to the stem.

5. The positioning system according to claim 1, wherein the at least one support device is mounted to the arm.

6. The positioning system according to claim 1, wherein the stem is mounted to the arm by a rotatable adjustment member.

7. The positioning system according to claim 6, wherein the rotatable adjustment member includes a channel configured to receive the stem, and
    wherein the stem is adjustable within the channel to adjust the height of the stem.

8. The positioning system according to claim 1, wherein the arm is rotatable between a storage position and a use position.

9. A positioning system for supporting a body of a user proximate to a worksite, the positioning system comprising:
    a base;
    an arm mounted to the base, the arm being rotatable between a storage position and a use position;
    at least one stabilizer fork housed within the base and operatively connected to the arm, said at least one stabilizer fork being moveable between a retracted position and an extended position;
    a stem mounted to the arm, the stem being moveable relative to the base; and
    at least one support device configured to support the body of the user, the stem and the at least one support device being configured to substantially align the body of the user along a neutral axis,
    wherein movement of the arm to the use position extends the at least one stabilizer fork and movement of the arm to the storage position retracts the at least one stabilizer fork.

10. The positioning system according to claim 1, wherein the at least one support device includes a lower leg support.

11. The positioning system according to claim 10, wherein the lower leg support is one of a shin support or a calf support.

12. A positioning system for supporting a body of a user proximate to a worksite, the positioning system comprising:
    a base;
    an arm mounted to the base, the arm being rotatable between a storage position and a use position;
    a stem mounted to the arm, the stem being moveable relative to the base; and
    one or more support devices configured to support the body of the user, the support devices comprising:
        a waist support configured to support a waist of the body of the user, the waist support being mounted to the stem; and
        a chest support configured to support a chest of the body of the user, the chest support being mounted to the stem separately from the waist support,
    wherein the stem and the support devices are configured to substantially align the body of the user along a neutral axis.

13. The positioning system according to claim 1, wherein the at least one support device includes an elbow/forearm support.

14. The positioning system according to claim 1, wherein the at least one support device includes a chest support.

15. A positioning system for supporting a body of a user proximate to a worksite, the positioning system comprising:
    a base;
    an arm mounted to the base, the arm being rotatable between a storage position and a use position;
    a stem mounted to the arm, the stem being moveable relative to the base; and
    one or more support devices configured to support the body of the user, the support devices comprising
        a chin support configured to support a chin of the body of the user, the chin support being mounted to the stem, wherein the stem and the support devices are configured to substantially align the body of the user along a neutral axis.

16. The positioning system according to claim 1, wherein the at least one support device includes a hamstring support.

17. The positioning system according to claim 15, wherein the support devices further comprise includes a chest support configured to support a chest of the body of the user, the chest support being mounted to the step separately from the chin support.

* * * * *